United States Patent
Zhong et al.

(10) Patent No.: US 10,759,809 B2
(45) Date of Patent: Sep. 1, 2020

(54) DEUTERATED COMPOUND AND MEDICAL USE THEREOF

(71) Applicant: Taizhou Huayuan Medicinal Tech Co. LTD., Taizhou, Jiangsu (CN)

(72) Inventors: Bohua Zhong, Beijing (CN); Jianming Wang, Beijing (CN); Jiajun Yang, Jiangsu (CN)

(73) Assignee: TAIZHOU HUAYUAN MEDICINAL TECH CO. LTD., Taizhou, Jiangsu (CN)

( * ) Notice: Subject to any disclaimer, the term of this patent is extended or adjusted under 35 U.S.C. 154(b) by 0 days.

(21) Appl. No.: 16/484,058

(22) PCT Filed: Jan. 26, 2018

(86) PCT No.: PCT/CN2018/000051
§ 371 (c)(1),
(2) Date: Aug. 6, 2019

(87) PCT Pub. No.: WO2018/141192
PCT Pub. Date: Aug. 9, 2018

(65) Prior Publication Data
US 2019/0389873 A1    Dec. 26, 2019

(30) Foreign Application Priority Data
Feb. 6, 2017    (CN) .......................... 2017 1 0063905

(51) Int. Cl.
| | |
|---|---|
| *C07D 489/12* | (2006.01) |
| *A61P 25/34* | (2006.01) |
| *A61P 25/36* | (2006.01) |
| *A61P 25/32* | (2006.01) |
| *A61K 45/06* | (2006.01) |

(52) U.S. Cl.
CPC ............ *C07D 489/12* (2013.01); *A61P 25/32* (2018.01); *A61P 25/34* (2018.01); *A61P 25/36* (2018.01); *A61K 45/06* (2013.01)

(58) Field of Classification Search
None
See application file for complete search history.

(56) References Cited

U.S. PATENT DOCUMENTS

| | | | |
|---|---|---|---|
| 8,703,099 | B2 | 4/2014 | Reis et al. |
| 9,175,000 | B2 | 11/2015 | Youngman |
| 2009/0082383 | A1 | 3/2009 | Czarnik |
| 2009/0208413 | A1 | 8/2009 | Reis et al. |
| 2014/0163058 | A1 | 6/2014 | Youngman |

FOREIGN PATENT DOCUMENTS

| | | |
|---|---|---|
| JP | 2016503754 A | 2/2016 |
| TW | 201434842 A | 9/2014 |
| WO | 2006091885 A2 | 8/2006 |
| WO | 2014087226 A1 | 6/2014 |

OTHER PUBLICATIONS

Polettini, Aldo et al. "Simultaneous determination of buprenorphine, norbuprenorphine, and buprenorphine-glucuronide in plasma by liquid chromatography—tandem mass spectrometry", Journal of Chromatography B, Feb. 12, 2001, p. 447-459, vol. 754, Elsevier, Chemistry and Drug Metabolism Section, IRP, NIDA, NIH, 5500 Nathan Shock Drive, Baltimore, MD 21224, USA, ISSN:0378-4347.

*Primary Examiner* — Noble E Jarrell
(74) *Attorney, Agent, or Firm* — Novick, Kim & Lee, PLLC; Allen Xue

(57) ABSTRACT

The present invention relates to a compound represented by formula I and a non-toxic pharmaceutically acceptable salt thereof. In formula (I), R1 is H, $CH_3$ or deuterated methyl ($CD_3$); R2 is $CH_3$ or $CH_2CH_3$; R3, R4 and R5 are each independently H or deuterium (D); when R1 is H or $CH_3$, at least one of R3, R4 and R5 is D.

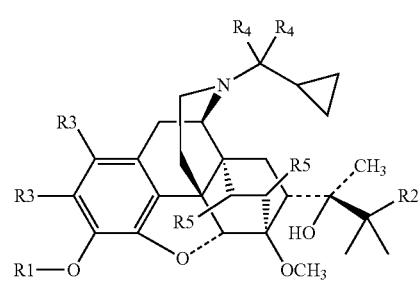

6 Claims, No Drawings

DEUTERATED COMPOUND AND MEDICAL USE THEREOF

TECHNICAL FIELD

Embodiments of the present invention relate to a novel deuterated N-cyclopropylmethyl-nororipavine derivative with an analgesic effect, a pharmaceutically acceptable salt thereof, a pharmaceutical composition containing the compound as an active ingredient, and the use of the derivative or a pharmaceutically acceptable salt thereof in the preparation of an analgesic.

BACKGROUND

The analgesic is one of the most commonly used drugs in the clinic. However, potent analgesics such as morphine and dulantin have strong potential for inducing dependence, which may cause addiction and tolerance while used for a long time; although non-narcotic analgesics have no potential for inducing dependence, the analgesic effect thereof are weak and insufficient to relieve severe pain in patients with cancer, trauma and surgery. Therefore, it is clinically necessary to provide a novel effective and safe analgesic.

Buprenorphine is the most commonly used analgesic and drug addiction eliminating medicine in the clinic; ADP2 is a buprenorphine analog that shows significantly higher analgesic activity and analgesic potency than buprenorphine (Master's thesis: Synthesis of buprenorphine analogs. 1999.6, graduate student: Wu Bo; instructor: Zhong Bohua). However, both buprenorphine and ADP2 have certain addictive properties, and are only effective for injection administration, which limits their clinical application. Continuously administration of buprenorphine in the clinic brings side effects of constipation.

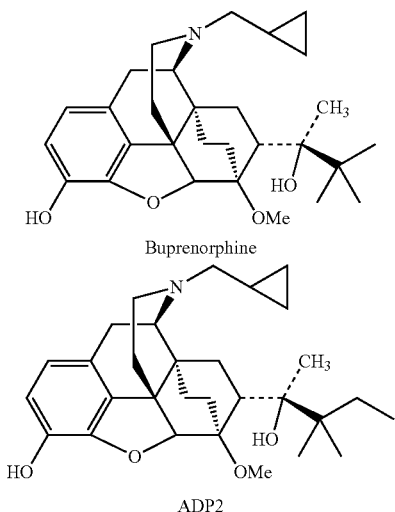
Buprenorphine

ADP2

The object of the present invention is to provide novel buprenorphine analogs that are orally effective and have low potential for inducing dependence.

SUMMARY

The present invention provides a compound represented by formula I and a non-toxic pharmaceutically acceptable salt thereof:

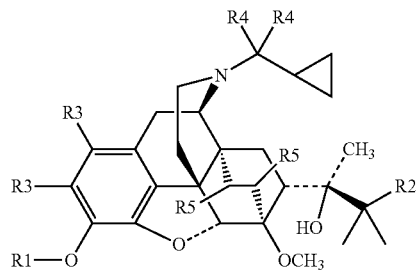

wherein, R1 is H, $CH_3$ or deuterated methyl ($CD_3$); R2 is $CH_3$ or $CH_2CH_3$; R3, R4 and R5 are each independently H or deuterium (D); when R1 is H or $CH_3$, at least one of R3, R4 and R5 is D.

The present invention provides a compound represented by Formula I and a non-toxic pharmaceutically acceptable salt thereof, wherein the compound is selected from the group consisting of:

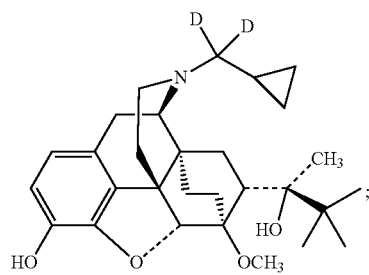

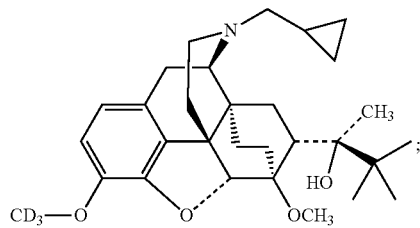

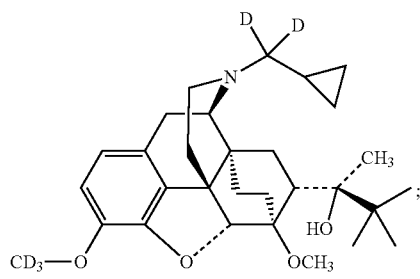

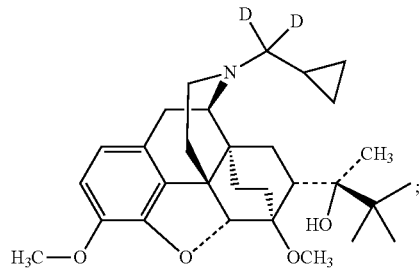

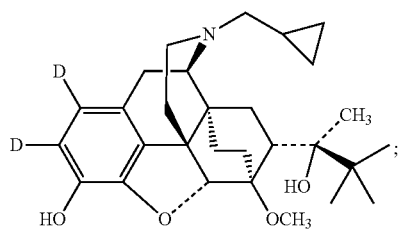
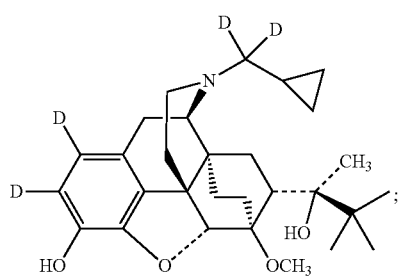
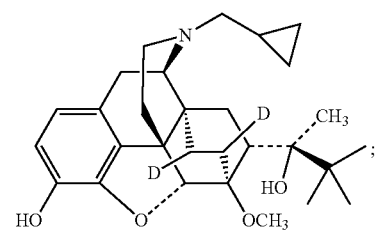
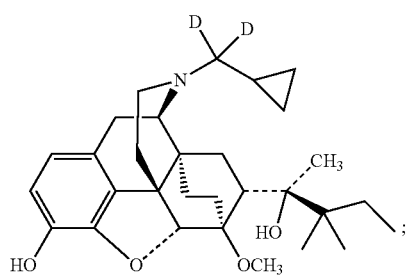
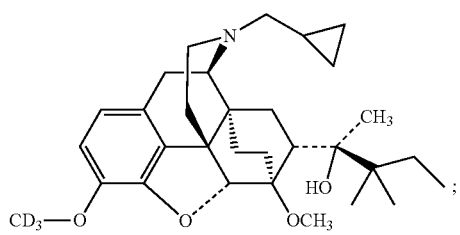
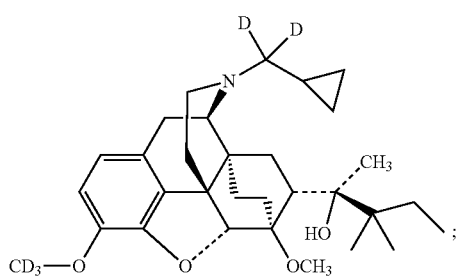

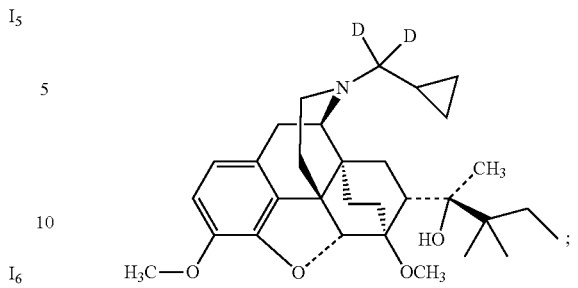
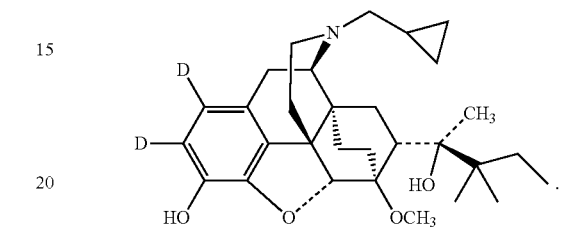

The present invention also provides a pharmaceutical composition comprising the compound represented by Formula I or a non-toxic pharmaceutically acceptable salt thereof as an active ingredient, and a suitable excipient. The pharmaceutical compositions may be solutions, tablets, capsules or injections; and the pharmaceutical compositions may be administered by injection or orally.

The invention also provides the use of the compound represented by Formula I, or a non-toxic pharmaceutically acceptable salt thereof for the preparation of a medicament for the treatment of algesic diseases.

Further, the present invention also provides the use of the compound represented by Formula I, or a non-toxic pharmaceutically acceptable salt thereof, for the preparation of a medicament for the treatment of algesic diseases or a medicament for the treatment of addictive diseases.

The present invention also provides a method for treating algesic diseases, wherein the method comprises administering an effective amount of the compound of Formula I, or a non-toxic pharmaceutically acceptable salt thereof or a pharmaceutical composition containing the compound.

The present invention also provides a method for treating addictive diseases, wherein the method comprises administering an effective amount of the compound of Formula I, or a non-toxic pharmaceutically acceptable salt or solvate thereof or the pharmaceutical composition containing the compound, The addictive disease is such as cocaine-induced addiction, methamphetamine addiction, opioid or drug addiction, alcohol addiction, smoking addiction, ketamine addiction.

The target compounds $I_{1-4}$ and $I_{8-11}$ can be prepared by the following synthetic route:

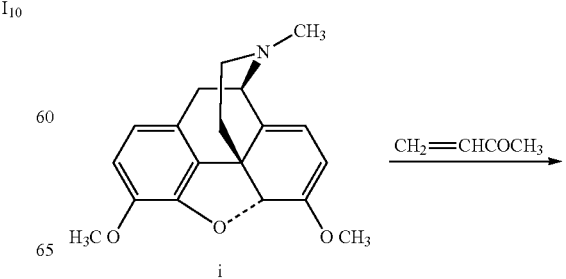

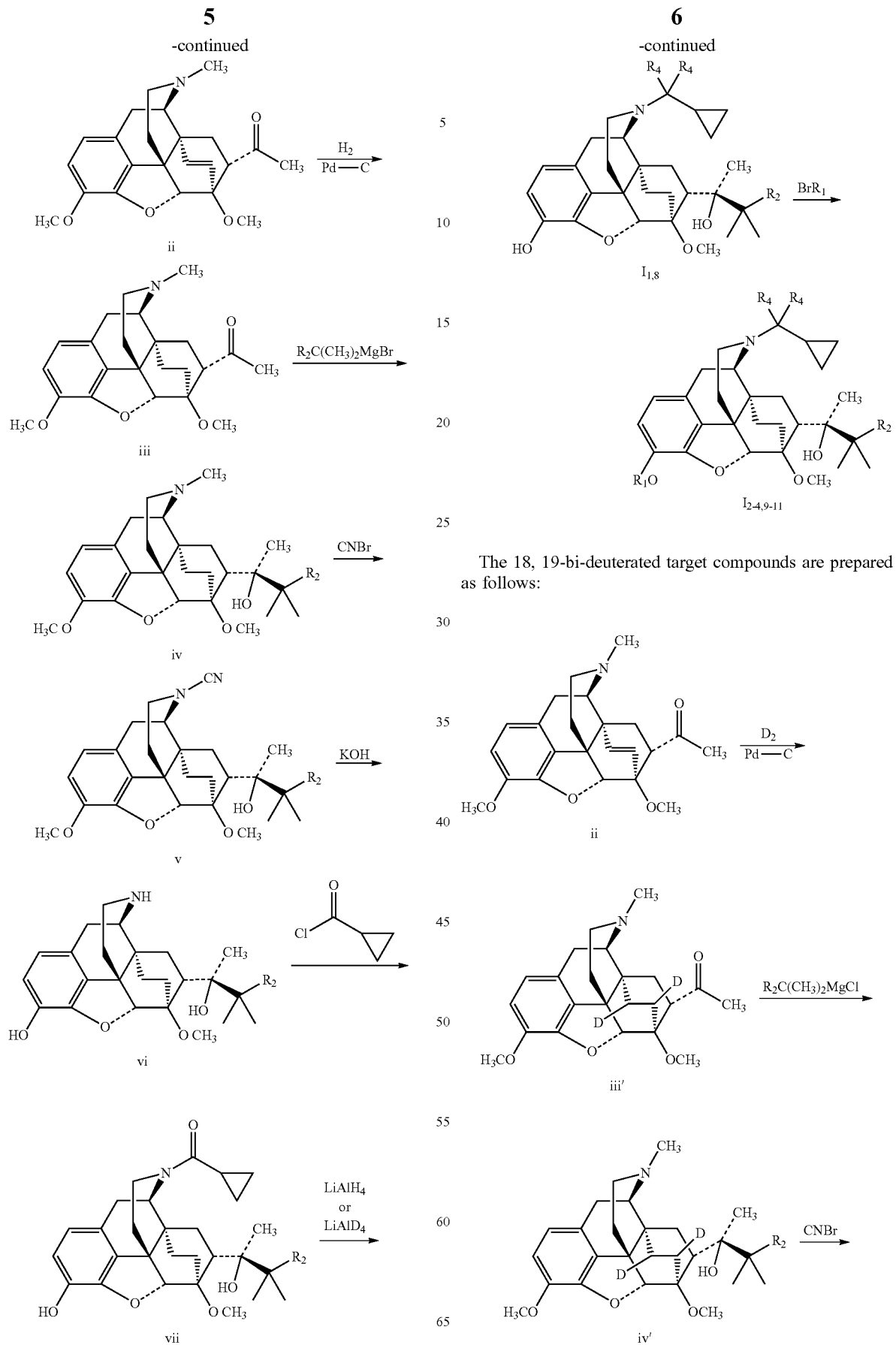
The 18, 19-bi-deuterated target compounds are prepared as follows:

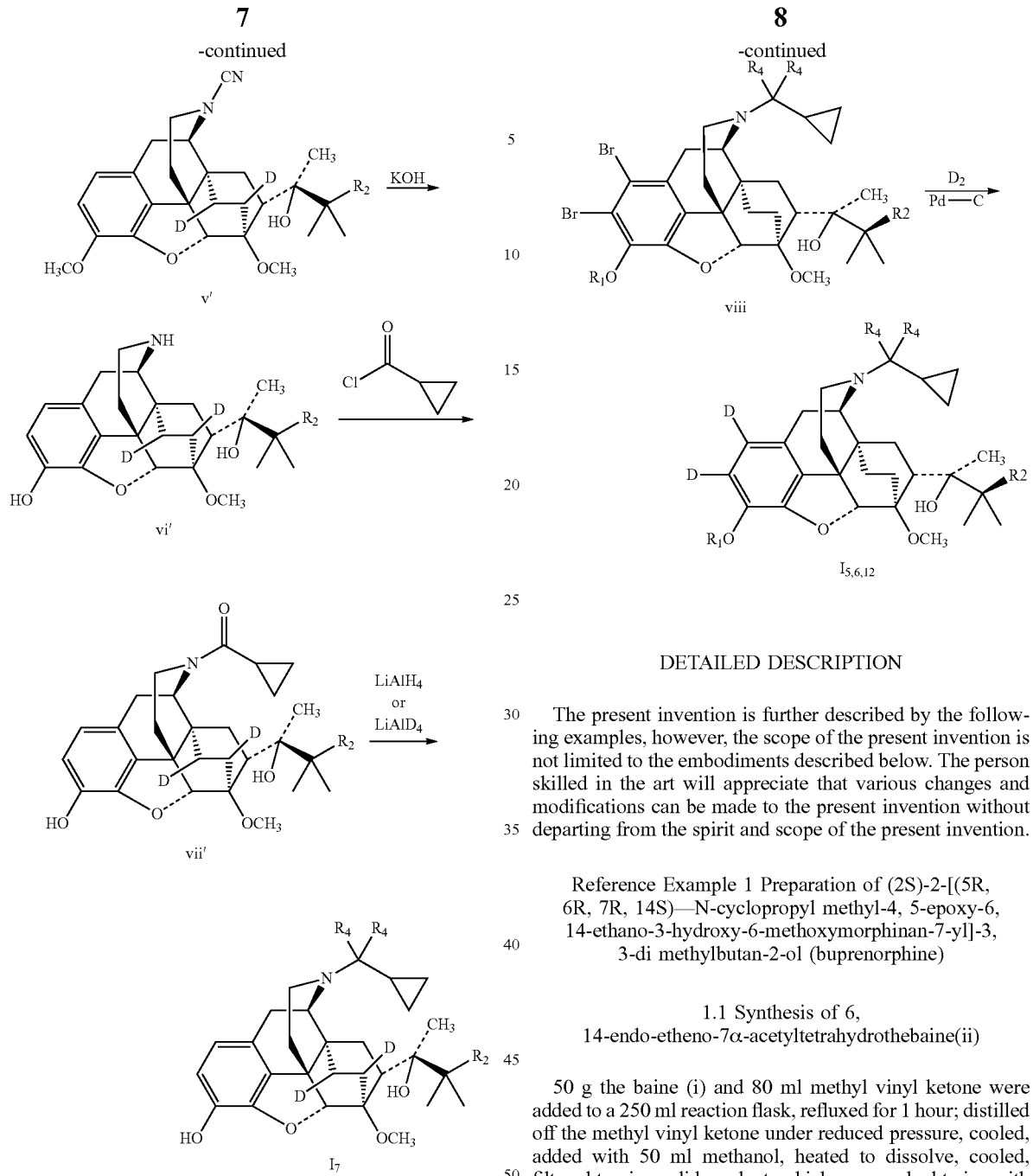

The compounds deuterated on the phenyl ring can be prepared as follows:

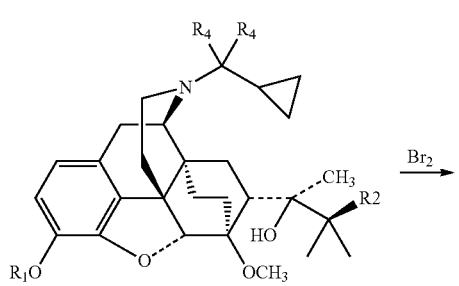

DETAILED DESCRIPTION

The present invention is further described by the following examples, however, the scope of the present invention is not limited to the embodiments described below. The person skilled in the art will appreciate that various changes and modifications can be made to the present invention without departing from the spirit and scope of the present invention.

Reference Example 1 Preparation of (2S)-2-[(5R, 6R, 7R, 14S)—N-cyclopropyl methyl-4, 5-epoxy-6, 14-ethano-3-hydroxy-6-methoxymorphinan-7-yl]-3, 3-di methylbutan-2-ol (buprenorphine)

1.1 Synthesis of 6, 14-endo-etheno-7α-acetyltetrahydrothebaine(ii)

50 g the baine (i) and 80 ml methyl vinyl ketone were added to a 250 ml reaction flask, refluxed for 1 hour; distilled off the methyl vinyl ketone under reduced pressure, cooled, added with 50 ml methanol, heated to dissolve, cooled, filtered to give solid product, which was washed twice with MeOH and dried to give 51 g ii, with the melting point of 118-121° C.

1.2 Synthesis of 7α-acetyl-6, 14-endo-ethanotetrahydrothebaine(iii)

20 g compound ii, 4 g 10% palladium carbon and 200 ml absolute ethanol were added to a vessel for hydrogenation, added with hydrogen gas at 40-50 kg/cm². The hydrogenation reaction was carried out at 50-60° C. for 8-12 hours, and after the reaction was completed, the reaction mixture was filtered with removal of the catalyst, concentrated to ⅓ volume under reduced pressure, cooled, filtered to give solid product, which was washed twice with anhydrous alcohol and dried to give 17 g iii, with the melting point of 134-137° C.

1.3 Synthesis of (2S)-2-[(5R,6R, 7R, 14S)—N-methyl-4,5-epoxy-6, 14-ethano-3-methoxy-6-methoxymorphinan-7-yl]-3,3-dimethylbutan-2-ol ($iv_1$)

0.5 g magnesium powder was added to 10 ml anhydrous diethyl ether, and added dropwise with a solution prepared by dissolving 1.2 g tert-butyl chloride (12 mmol) in a mixed solvent of 15 ml anhydrous diethyl ether and 10 ml anhydrous benzene while stirring to obtain a Grignard reagent; A solution of 4 g (10 mmol) iii dissolved in 30 mL diethyl ether-benzene (1:1) was added dropwise to the Grignard reagent, after the completion of the addition, stirred and refluxed for 6 hours; After the completion of the reaction, the mixture was cooled in an ice bath, added dropwise with 15 mL saturated ammonium chloride solution, and filtered. The filtrate was allowed to stand, and the organic layer was separated. The aqueous layer was extracted with diethyl ether (25 ml×4). The organic phase was combined and washed with water to neutral, dried with anhydrous sodium sulfate overnight, vaporated under reduced pressure with the removal of solvent, separated by silica gel chromatography using a mixture of dichloromethane:petroleum ether:methanol (2:7:1) as an eluent. The desired fractions were collected, and evaporated to dryness to give 3.7 g pale yellow solid.

1.4 Synthesis of (2S)-2-[(5R, 6R, 7R, 14S)—N-cyano-4, 5-epoxy-6,14-ethano-3-methoxy-6-methoxymorphinan-7-yl]-3, 3-dimethylbutan-2-ol ($v_1$)

1.5 g cyanogen bromide was dissolved in 15 ml chloroform, and added dropwise a solution of 3.7 g $iv_1$ dissolved in 25 ml chloroform while stirring, refluxed for 12 hr. After completion of the reaction, the solution was evaporated with the removal of solvent, treated with a small amount of anhydrous ethanol to give 3.8 g white powder $v_1$.

1.5 Synthesis of (2S)-2-[(5R, 6R, 7R, 14S)-4,5-epoxy-6,14-ethano-3-hydroxy-6-methoxymorphinan-7-yl]-3,3-dimethylbutan-2-ol ($vi_1$)

10 g potassium hydroxide was added to 25 ml diethylene glycol, added with nitrogen gas, heated to 100° C. while stirring; then added with 3.8 g $v_1$, heated at 190 to 200° C. for 1 hour, and poured into ice water. The reaction mixture was neutralized to pH 8-9 by adding a saturated aqueous solution of ammonium chloride, filtered to obtain the solid, which was separated by silica gel chromatography using a mixture of dichloromethane:petroleum ether:methanol (2:7:1) as an eluent. The desired fractions were collected, and evaporated to dryness to give 3.2 g $vi_1$ with the melting point higher than 200° C.

1.6 Synthesis of (2S)-2-[(5R, 6R, 7R, 14S)—N-cyclopropanoyl-4, 5-epoxy-6,14-ethano-3-hydroxy-6-methoxymorphinan-7-yl]-3, 3-dimethylbutan-2-ol ($vii_1$)

3.2 g (7.7 mmol) of $vi_1$, 0.9 g triethylamine were added to 25 ml anhydrous dichloromethane, and dissolved while stirring; added with 0.8 g (7.7 mmol) cyclopropanoyl chloride dropwise in an ice bath. After the addition was completed, the mixture was further stirred to react in an ice bath for 8 hours, then stirred at room temperature for 5 hours, and filtered. The filtrate was evaporated to dryness under reduced pressure, and separated by silica gel column chromatography using a mixture of dichloromethane:petroleum ether:methanol (2:7:1) as an eluent. The desired fractions were collected, and evaporated to dryness to give 1.7 g $vii_1$.

1.7 Preparation of Buprenorphine 0.96 g (2 mmol) vii1 was dissolved in 5 ml anhydrous tetrahydrofuran, added dropwise with 2 ml 2M solution of $LiAlH_4$ in tetrahydrofuran while stirring; After the completion of the addition, the mixture was stirred at room temperature overnight; then added with magnesium sulfate heptahydrate in portions until no gas evolved, and filtered. The filtrate was evaporated to dryness under reduced pressure, and separated by silica gel column chromatography using a mixture of petroleum ether:dichloromethane:methanol=4:1:0.1 as an eluent. The desired fractions were collected, recrystallized from methanol to give 0.72 g white solid of buprenorphine, which was dissolved in ethanol, added with a solution of hydrogen chloride in ether to pH=2, stirred, precipitated a solid, kept standing overnight, then filtered, washed with anhydrous ether to obtain 0.68 g buprenorphine .HCl with the melting point higher than 200° C. $^1$H-NMR (400 MHz, DMSO-d6): 9.65 (br, 1H); 9.40 (br, 1H); 6.74 (d, 1H); 6.56 (d, 1H); 4.66 (br, 1H); 4.55 (s, 1H); 3.91 (d, 1H); 3.42 (s, 3H); 3.29 (m, 2H); 3.20 (m, 2H); 2.90 m, 1H); 2.80 (m, 2H); 2.29 (m, 1H); 1.95 (m, 2H); 1.83 (m, 2H); 1.71 (m, 1H); 1.45 (m, 1H); 1.34 (m, 1H); 1.31 (s, 3H); 1.02 (s, 9H); 0.68 (m, 2H); 0.61 (m, 2H); 0.40 (m, 1H).

Reference Example 2 Preparation of (2S)-2-[(5R, 6R, 7R, 14S)—N-cyclopropylmethyl-4, 5-epoxy-6, 14-ethano-3-hydroxy-6-methoxymorphinan-7-yl]-3, 3-dimethylpentan-2-ol (ADP2)

Referring to the method of reference example 1.3, 2-chloro-2-methylbutane was substituted for tert-butyl chloride to carry out Grignard addition react ion with iii to prepare (2S)-2-[(5R, 6R, 7R, 14S)—N-methyl-4, 5-epoxy-6,14-ethano-3-methoxy-6-methoxymorphinan-7-yl]-3, 3-dimethyl pentan-2-ol ($iv_2$).

Referring to the method of reference example 1.4, $iv_2$ was substituted for $iv_1$ to react with cyanogen bromide to obtain (2S)-2-[(5R,6R, 7R,14S)—N-cyano-4,5-epoxy-6,14-ethano-3-methoxy-6-methoxymorphinan-7-yl]-3,3-dimethylpentan-2-ol ($v_2$).

Referring to the method of reference example 1.5, $v_2$ was substituted for $v_1$ to react with potassium hydroxide to obtain (2S)-2-[(5R, 6R, 7R, 14S)-4,5-epoxy-6,14-ethano-3-hydroxy-6-methoxymorphinan-7-yl]-3,3-dimethylpentan-2-ol ($vi_2$).

Referring to the method of reference example 1.6, $vi_2$ was substituted for $vi_1$ to react with cyclopropanecarbonyl chloride to obtain (2S)-2-[(5R, 6R, 7R, 14S)—N-cyclopropanoyl-4, 5-epoxy-6, 14-ethano-3-hydroxy-6-methoxymorphinan-7-yl]-3, 3-dimethylpentan-2-ol ($vii_2$).

Referring to the method of reference example 1.7, $vii_2$ was substituted for $vii_1$ to react with $LiAlH_4$ to obtain 0.58 g ADP2; ADP2 was dissolved in ethanol, added with a solution of hydrogen chloride in ether to pH=2, stirred, and precipitated a solid, kept standing overnight, filtered and wash with anhydrous ether to give 0.43 g ADP2.HCl with the melting point higher than 200° C. Nuclear magnetic resonance spectroscopy: $^1$H-NMR (400 MHz, DMSO-d6): 9.62 (br, 1H); 9.39 (br, 1H); 6.73 (d, 1H); 6.55 (d, 1H); 4.64 (br, 1H); 4.54 (s, 1H); 3.90 (d, 1H); 3.41 (s, 3H); 3.28 (m, 2H); 3.20 (m, 2H); 2.88 (m, 1H); 2.79 (m, 2H); 2.28 (m, 1H); 1.96 (m, 2H); 1.82 (m, 2H); 1.70 (m, 1H); 1.47 (m, 1H); 1.35

(m, 1H); 1.30 (s, 3H); 1.23 (q, 2H); 1.03 (s, 6H); 0.98 (t, 3H); 0.67 (m, 2H); 0.60 (m, 2H); 0.39 (m, 1H).

Example 1 Preparation of (2S)-2-[(5R, 6R, 7R, 14S)—N-(cyclopropyl-dideuteromethyl)-4, 5-epoxy-6, 14-ethano-3-hydroxy-6-methoxymorphinan-7-yl]-3, 3-dimethylbutan-2-ol (I₁)

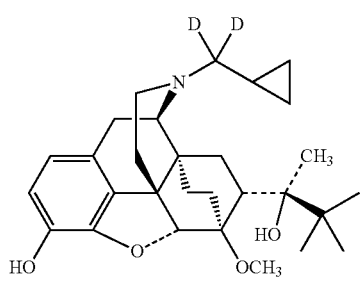

I₁

Referring to the method of reference example 1.7, vii₁ was reacted with LiAlD₄ (% D: >98) to obtain I₁; I1 was dissolved in ethanol and salted with hydrogen chloride to obtain I₁.HCl with the melting point: >200° C. ¹H-NMR (400 MHz, DMSO-d6): 9.70 (br, 1H); 9.43 (br, 1H); 6.75 (d, 1H); 6.58 (d, 1H); 4.71 (br, 1H); 4.53 (s, 1H); 3.92 (d, 1H); 3.42 (s, 3H); 3.29 (m, 2H); 2.90 m, 1H); 2.80 (m, 2H); 2.29 (m, 1H); 1.95 (m, 2H); 1.83 (m, 2H); 1.70 (m, 1H); 1.44 (m, 1H); 1.32 (m, 1H); 1.31 (s, 3H); 1.02 (s, 9H); 0.69 (m, 2H); 0.62 (m, 2H); 0.40 (m, 1H).

Example 2 Preparation of (2S)-2-[(5R, 6R, 7R, 14S)—N-cyclopropylmethyl-4,5-epoxy-6, 14-ethano-3-trisdeuterated-methyloxy-6-methoxy-morphinan-7-yl]-3,3-dimethylbutan-2-ol (I₂)

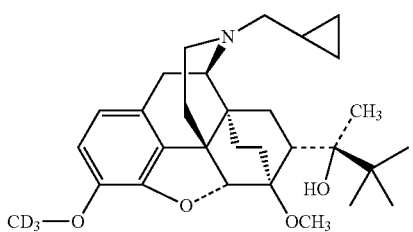

I₂

0.47 g (1 mmol) buprenorphine was added to 5 ml dimethylformamide and dissolved by stirring; then added with 280 mg (2 mmol) potassium carbonate, added dropwise with 290 mg (% D: >98, 2 mmol) CD₃I while stirring, stirred to react at 50° C. for 15 hours. The solid was filtered off and the filtrate was evaporated to dryness under reduced pressure. The mixture was separated by silica gel column chromatography using a mixture of dichloromethane:petroleum ether:methanol (2:7:1) as an eluent. The desired fractions were collected, and evaporated to dryness under reduced pressure to give 430 mg I₂. I₂ was dissolved in ethanol and salted with hydrogen chloride to obtain I₂.HCl with the melting point: >200° C. ¹H-NMR (400 MHz, DMSO-d6): 9.56 (br, 1H); 6.78 (d, 1H); 6.59 (d, 1H); 4.67 (br, 1H); 4.54 (s, 1H); 3.91 (d, 1H); 3.42 (s, 3H); 3.29 (m, 2H); 3.20 (m, 2H); 2.90 m, 1H); 2.80 (m, 2H); 2.29 (m, 1H); 1.95 (m, 2H); 1.83 (m, 2H); 1.71 (m, 1H); 1.45 (m, 1H); 1.34 (m, 1H); 1.30 (s, 3H); 1.01 (s, 9H); 0.67 (m, 2H); 0.60 (m, 2H); 0.39 (m, 1H).

Example 3 Preparation of (2S)-2-[(5R, 6R, 7R, 14S)—N-(cyclopropyl-dideuteromethyl)-4,5-epoxy-6,14-ethano-3-trideuterated methyloxy-6-methoxy-morphinan-7-yl]-3,3-dimethylbutan-2-ol (I₃)

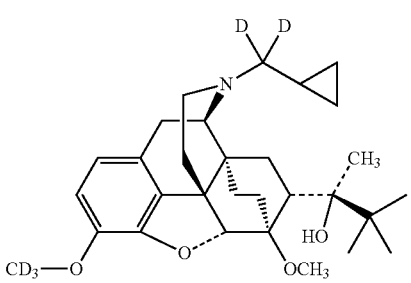

I₃

Referring to the method of example 2, I₁ was substituted for buprenorphine to react with CD₃I to obtain 13; 13 was dissolved in ethanol and salted with hydrogen chloride to obtain I₃.HCl with the melting point: >200° C. ¹H-NMR (400 MHz, DMSO-d6): 9.60 (br, 1H); 6.79 (d, 1H); 6.60 (d, 1H); 4.68 (br, 1H); 4.56 (s, 1H); 3.92 (d, 1H); 3.42 (s, 3H); 3.29 (m, 2H); 2.90 m, 1H); 2.80 (m, 2H); 2.29 (m, 1H); 1.95 (m, 2H); 1.83 (m, 2H); 1.71 (m, 1H); 1.45 (m, 1H); 1.34 (m, 1H); 1.31 (s, 3H); 1.03 (s, 9H); 0.68 (m, 2H); 0.60 (m, 2H); 0.41 (m, 1H).

Example 4 Preparation of (2S)-2-[(5R, 6R, 7R, 14S)—N-(cyclopropyl-dideuteromethyl)-4, 5-epoxy-6,14-ethano-3-methoxy-6-methoxymorphinan-7-yl]-3,3-dimethylbutan-2-ol (I₄)

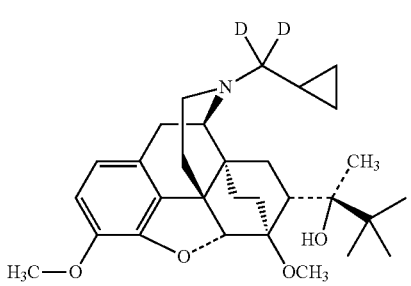

I₄

Referring to the method of example 2, I₁ was substituted for buprenorphine to react with CH₃I to obtain I₄; I₄ was dissolved in ethanol and salted with hydrogen chloride to obtain I₄.HCl with the melting point: >200° C. ¹H-NMR (400 MHz, DMSO-d6): 9.58 (br, 1H); 6.77 (d, 1H); 6.59 (d, 1H); 4.82 (br, 1H); 4.55 (s, 1H); 3.91 (d, 1H); 3.85 ((s, 3H); 3.42 (s, 3H); 3.26 (m, 2H); 2.87 m, 1H); 2.75 (m, 2H); 2.26 (m, 1H); 1.92 (m, 2H); 1.81 (m, 2H); 1.70 (m, 1H); 1.45 (m, 1H); 1.34 (m, 1H); 1.31 (s, 3H); 1.02 (s, 9H); 0.68 (m, 2H); 0.61 (m, 2H); 0.41 (m, 1H).

Example 5 Preparation of (2S)-2-[(5R, 6R, 7R, 14S)-1, 2-dideutero-N-cyclopropylmethyl-4,5-epoxy-6,14-ethano-3-hydroxy-6-methoxymorphinan-7-yl]-3, 3-dimethylbutan-2-ol ($I_5$)

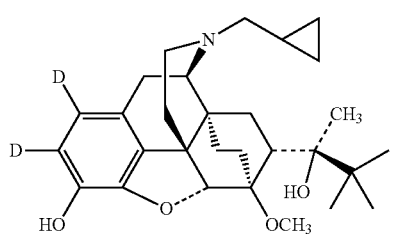

0.3 g buprenorphine was added to 5 ml dichloromethane, dissolved by stirring; added dropwise with a solution of 60 μl bromine in 1 ml dichloromethane in an ice bath; After the completion of the addition, the temperature was raised to 30° C., and the mixture was stirred to react for 1 hour. The reaction mixture was washed with water and then a saturated aqueous solution of sodium hydrogen carbonate. The organic layer was separated and dried over anhydrous sodium sulfate. The solid was filtered off and the filtrate was evaporated to dryness under reduced pressure. The mixture was separated by silica gel column chromatography using a mixture of dichloromethane:petroleum ether:methanol (2:7:1) as an eluent. The desired fractions were collected, and evaporated to dryness to give 41 mg (2S)-2-[(5R, 6R, 7R, 14S)-1,2-dibromo-N-cyclopropylmethyl-4,5-epoxy-6,14-ethylene-3-hydroxy-6-methoxymorphinan-7-yl]-3,3-dimethylbutyl-2-alcohol ($viii_1$).

41 mg $viii_1$ was dissolved in 0.5 ml anhydrous tetrahydrofuran, added with 20 μl anhydrous triethylamine and 20 mg 10% Pd—C, with the reaction flask connected to a high vacuum system and deuterium gas fed, stirred at room temperature for 24 hours. The solid was filtered off and the filtrate was evaporated to dryness under reduced pressure. The mixture was petroleum ether: by silica gel column chromatography using a mixture of dichloromethane:petroleum ether:methanol (2:7:1) as an eluent. The desired fractions were collected, and evaporated to dryness to give 19 mg $I_5$. $I_5$ was dissolved in ethanol and salted with hydrogen chloride to obtain $I_5$.HCl with the melting point: >200° C. $^1$H-NMR (400 MHz, DMSO-d6): 9.60 (br, 1H); 9.43 (br, 1H); 4.72 (br, 1H); 4.55 (s, 1H); 3.91 (d, 1H); 3.42 (s, 3H); 3.32 (m, 2H); 3.25 (m, 2H); 2.92 m, 1H); 2.83 (m, 2H); 2.31 (m, 1H); 1.97 (m, 2H); 1.86 (m, 2H); 1.74 (m, 1H); 1.46 (m, 1H); 1.34 (m, 1H); 1.31 (s, 3H); 1.00 (s, 9H); 0.69 (m, 2H); 0.61 (m, 2H); 0.40 (m, 1H).

Example 6 Preparation of (2S)-2-[(5R, 6R, 7R, 14S)-1,2-dideutero-N-(cyclopropyl-dideuteromethyl)-4, 5-epoxy-6,14-ethano-3-hydroxy-6-methoxymorphinan-7-yl]-3, 3-dimethylbutan-2-ol ($I_6$)

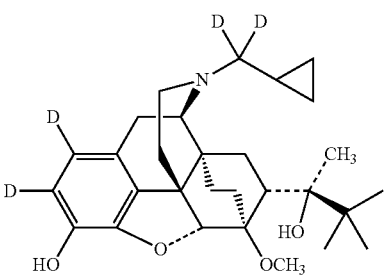

Referring to the method of example 5, $I_1$ was substituted for buprenorphine to carry out the bromination reaction to obtain (2S)-2-[(5R,6R,7R,14S)-1,2-dibromo-N-(cyclopropane-dideuteromethyl)-4,5-epoxy-6,14-ethano-3-hydroxy-6-methoxymorphinan-7-yl]-3,3-dimethylbutan-2-ol ($viii_2$); $viii_2$ was substituted for $viii_1$ to carry out deuteration reaction to obtain 16; 16 was dissolved in ethanol and salted with hydrogen chloride to obtain $I_6$.HCl with the melting point: >200° C. $^1$H-NMR (400 MHz, DMSO-d6): 9.72 (br, 1H); 9.42 (br, 1H); 4.69 (br, 1H); 4.55 (s, 1H); 3.91 (d, 1H); 3.41 (s, 3H); 3.28 (m, 2H); 2.92 m, 1H); 2.83 (m, 2H); 2.32 (m, 1H); 1.98 (m, 2H); 1.86 (m, 2H); 1.73 (m, 1H); 1.47 (m, 1H); 1.35 (m, 1H); 1.31 (s, 3H); 1.01 (s, 9H); 0.68 (m, 2H); 0.61 (m, 2H); 0.40 (m, 1H).

Example 7 Preparation of (2S)-2-[(5R, 6R, 7R, 14S)—N-(cyclopropyl-methyl)-4, 5-epoxy-6,14-dideuteroethano-3-hydroxy-6-methoxymorphinan-7-yl]-3,3-dimethylbutan-2-ol ($I_7$)

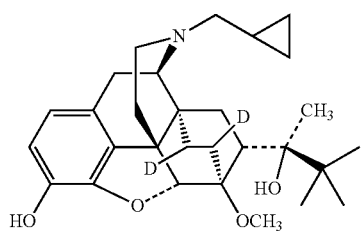

Referring to the method of reference example 1.2, ii was subjected to a deuteration addition reaction under deuterium gas substituting for hydrogen gas to obtain 7α-acetyl-6, 14-dideuteroethyl bridge tetrahydrothebaine (iii').

Referring to the method of reference example 1.3, iii' was substituted for iii, to carry out a Grignard addition with the Grignard reagent of tert-butyl chloride to prepare (2S)-2-[(5R, 6R, 7R, 14S)—N-methyl-4, 5-epoxy-6,14-dideuteroethano-3-methoxy-6-methoxymorphinan-7-yl]-3, 3-dimethylbutan-2-ol (iv').

Referring to the method of reference example 1.4, iv' was substituted for $iv_1$, to react with cyanogen bromide to obtain (2S)-2-[(5R,6R,7R,14S)—N-cyano-4,5-epoxy-6,14-dideuteroethano-3-methoxy-6-methoxymorphinan-7-yl]-3,3-dimethylbutan-2-ol (v').

Referring to the method of reference example 1.5, v' was substituted for $v_1$ to react with potassium hydroxide to obtain (2S)-2-[(5R, 6R, 7R, 14S)-4, 5-epoxy-6, 14-dideuteroethano-3-hydroxy-6-methoxymorphinan-7-yl]-3, 3-dimethylbutan-2-ol (vi').

Referring to the method of reference example 1.6, vi' was substituted for $vi_1$ to react with cyclopropanecarbonyl chloride to obtain (2S)-2-[(5R,6R,7R, 14S)—N-cyclopropanecarbonyl-4, 5-epoxy-6, 14-dideuteroethano-3-hydroxy-6-methoxymorphinan-7-yl]-3,3-dimethylbutan-2-ol (vii').

Referring to the method of reference example 1.7, vii' was substituted for viii to react with LiAlH$_4$ to obtain 17; 17 was dissolved in ethanol and salted with hydrogen chloride to obtain $I_7$.HCl with the melting point: >200° C. $^1$H-NMR (400 MHz, DMSO-d6): 9.62 (br, 1H); 9.41 (br, 1H); 6.73 (d, 1H); 6.55 (d, 1H); 4.62 (br, 1H); 4.56 (s, 1H); 3.91 (d, 1H); 3.40 (s, 3H); 3.29 (m, 2H); 3.20 (m, 2H); 2.90 m, 1H); 2.80 (m, 2H); 2.29 (m, 1H); 1.83 (m, 2H); 1.71 (m, 1H); 1.30 (s, 3H); 1.03 (s, 9H); 0.68 (m, 2H); 0.61 (m, 2H); 0.40 (m, 1H).

Example 8 Preparation of (2S)-2-[(5R, 6R, 7R, 14S)—N-(cyclopropyl-dideuteromethyl)-4, 5-epoxy-6,14-ethano-3-hydroxy-6-methoxymorphinan-7-yl]-3,3-dimethylpentan-2-ol ($I_8$)

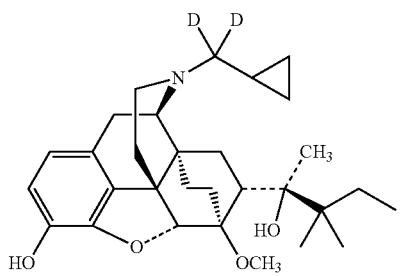

$I_8$

Referring to the method of reference example 1.7, vii$_2$ was reacted with LiAlD$_4$ to obtain 18; 18 was dissolved in ethanol and salted with hydrogen chloride to obtain $I_8$.HCl, melting point: >200° C. $^1$H-NMR (400 MHz, DMSO-d6): 9.62 (br, 1H); 9.39 (br, 1H); 6.73 (d, 1H); 6.55 (d, 1H); 4.64 (br, 1H); 4.54 (s, 1H); 3.90 (d, 1H); 3.41 (s, 3H); 3.28 (m, 2H); 3.20 (m, 2H); 2.88 (m, 1H); 2.79 (m, 2H); 2.28 (m, 1H); 1.96 (m, 2H); 1.82 (m, 2H); 1.70 (m, 1H); 1.47 (m, 1H); 1.35 (m, 1H); 1.30 (s, 3H); 1.23 (q, 2H); 1.03 (s, 6H); 0.98 (t, 3H); 0.67 (m, 2H); 0.60 (m, 2H); 0.39 (m, 1H).

Example 9 Preparation of (2S)-2-[(5R, 6R, 7R, 14S)—N-cyclopropylmethyl-4,5-epoxy-6, 14-ethano-3-trisdeuteromethyloxy-6-methoxymorphinan-7-yl]-3, 3-dimethylpentan-2-ol (19)

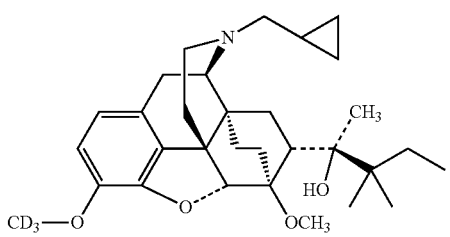

$I_9$

Referring to the method of example 2, ADP2 was substituted for buprenorphine to react with CD$_3$I to obtain 19; 19 was dissolved in ethanol and salted with hydrogen chloride to obtain $I_9$.HCl with the melting point: >200° C. $^1$H-NMR (400 MHz, DMSO-d6): 9.51 (br, 1H); 6.78 (d, 1H); 6.59 (d, 1H); 4.65 (br, 1H); 4.54 (s, 1H); 3.90 (d, 1H); 3.41 (s, 3H); 3.31 (m, 2H); 3.24 (m, 2H); 2.90 (m, 1H); 2.82 (m, 2H); 2.29 (m, 1H); 1.99 (m, 2H); 1.82 (m, 2H); 1.70 (m, 1H); 1.47 (m, 1H); 1.35 (m, 1H); 1.30 (s, 3H); 1.23 (q, 2H); 1.06 (s, 6H); 0.98 (t, 3H); 0.67 (m, 2H); 0.60 (m, 2H); 0.39 (m, 1H).

Example 10 Preparation of (2S)-2-[(5R, 6R, 7R, 14S)—N-(cyclopropyl-dideuteromethyl)-4,5-epoxy-6,14-ethano-3-trideuteromethyloxy-6-methoxymorphinan-7-yl]-3, 3-dimethylpentan-2-ol ($I_{10}$)

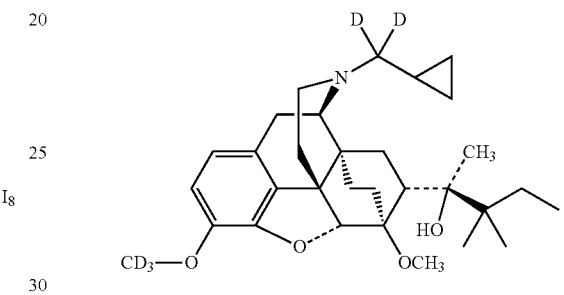

$I_{10}$

Referring to the method of example 2, 18 was substituted for buprenorphine to react with CD$_3$I to obtain $I_{10}$; $I_{10}$ was dissolved in ethanol and salted with hydrogen chloride to obtain $I_{10}$.HCl with the melting point: >200° C. $^1$H-NMR (400 MHz, DMSO-d6): 9.40 (br, 1H); 6.78 (d, 1H); 6.58 (d, 1H); 4.69 (br, 1H); 4.54 (s, 1H); 3.90 (d, 1H); 3.40 (s, 3H); 3.25 (m, 2H); 2.86 (m, 1H); 2.77 (m, 2H); 2.26 (m, 1H); 1.956 (m, 2H); 1.82 (m, 2H); 1.70 (m, 1H); 1.47 (m, 1H); 1.31-1.30 (m, 4H); 1.24 (q, 2H); 1.05 (s, 6H); 0.97 (t, 3H); 0.67 (m, 2H); 0.61 (m, 2H); 0.42 (m, 1H).

Example 11 Preparation of (2S)-2-[(5R, 6R, 7R, 14S)—N-(cyclopropyl-dideuteromethyl)-4, 5-epoxy-6, 14-ethano-3-methoxy-6-methoxymorphinan-7-yl]-3, 3-dimethylpentan-2-ol ($I_{11}$)

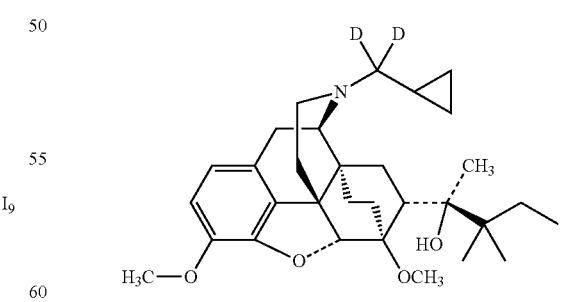

$I_{11}$

Referring to the method of example 2, 18 was substituted for buprenorphine to react with CH$_3$I to obtain $I_{11}$; $I_{11}$ was dissolved in ethanol and salted with hydrogen chloride to obtain $I_{11}$.HCl with the melting point: >200° C. $^1$H-NMR (400 MHz, DMSO-d6): 9.49 (br, 1H); 6.77 (d, 1H); 6.58 (d, 1H); 4.64 (br, 1H); 4.54 (s, 1H); 3.90 (d, 1H); 3.86 (s, 3H);

3.42 (s, 3H); 3.25 (m, 2H); 2.86 (m, 1H); 2.78 (m, 2H); 2.29 (m, 1H); 1.96 (m, 2H); 1.82 (m, 2H); 1.70 (m, 1H); 1.47 (m, 1H); 1.37 (m, 1H); 1.31 (s, 3H); 1.23 (q, 2H); 1.03 (s, 6H); 0.98 (t, 3H); 0.67 (m, 2H); 0.60 (m, 2H); 0.39 (m, 1H).

Example 12 Preparation of (2S)-2-[(5R, 6R, 7R, 14S)-1,2-dideutero-N-cyclopropylmethyl-4,5-epoxy-6,14-ethano-3-hydroxy-6-methoxymorphinan-7-yl]-3, 3-dimethylpentan-2-ol ($I_{12}$)

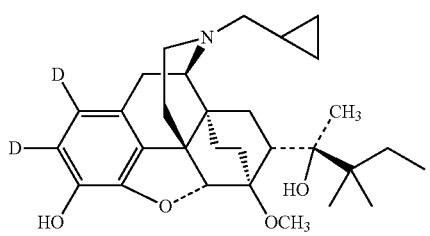

$I_{12}$

Referring to the method of example 5, ADP2 was substituted for buprenorphine to carrying out the bromination reaction to obtain (2S)-2-[(5R, 6R, 7R, 14S)-1, 2-dibromo-N-cyclopropylmethyl-4,5-epoxy-6,14-ethano-3-hydroxy-6-methoxymorphinan-7-yl]-3,3-dimethylpentan-2-ol ($viii_3$); $viii_3$ was substituted for $viii_1$ to carry out the deuteration reaction to obtain $I_{12}$; $I_{12}$ was dissolved in ethanol and salted with hydrogen chloride to obtain $I_{12}$·HCl with the melting point: >200° C. $^1$H-NMR (400 MHz, DMSO-d6): 9.62 (br, 1H); 9.39 (br, 1H); 4.64 (br, 1H); 4.54 (s, 1H); 3.90 (d, 1H); 3.43 (s, 3H); 3.26 (m, 2H); 3.17 (m, 2H); 2.86 (m, 1H); 2.79 (m, 2H); 2.28 (m, 1H); 1.96 (m, 2H); 1.82 (m, 2H); 1.70 (m, 1H); 1.47 (m, 1H); 1.35 (m, 1H); 1.32 (s, 3H); 1.23 (q, 2H); 1.01 (s, 6H); 0.99 (t, 3H); 0.68 (m, 2H); 0.62 (m, 2H); 0.40 (m, 1H).

Example 13 Determination of Analgesic Activity by Hot Plate Assay of Mice

While Kunming mice, male, were placed on a hot plate at 55° C., the time was calculated immediately until the mice licked or stamped their hind paws for the first time. The calculated time was recorded as the pre-administration basal pain threshold; then the mice were randomized to 10 animals per group; Each mouse was administered by gavage, placed on a hot plate at 55° C. 1 hour after administration and the time was calculated until the mice licked or stamped their hind paws for the first time. The time calculated was recorded as the post-administration pain threshold; It was recorded as 100% of analgesia without the occurrence of licking or stamping hind paws in 60 seconds. The percentage of analgesia was calculated by comparison of the pain threshold before and after administration, and the calculation formula was as follows:

$$\text{analgesia \%} = \frac{\text{post-administration pain threshold} - \text{pre-administration pain threshold}}{60 \text{ s} - \text{pre-administration pain threshold}} \times 100\%$$

The $ED_{50}$ value was calculated using the bliss method. The results are shown in Table 1:

TABLE 1

Determination of analgesic activity by hot plate assay of mice

| Drug | $ED_{50}$ (mg/kg) |
|---|---|
| buprenorphine·HCl | 11.82 ± 11.73 |
| ADP2·HCl | 2.60 ± 3.77 |
| $I_1$·HCl | 6.54 ± 2.96 |
| $I_2$·HCl | 19.28 ± 17.00 |
| $I_3$·HCl | 21.10 ± 2.87 |
| $I_4$·HCl | 4.61 ± 2.03 |
| $I_5$·HCl | 8.02 ± 11.34 |
| $I_6$·HCl | 5.83 ± 2.23 |
| $I_7$·HCl | 12.02 ± 11.67 |
| $I_8$·HCl | 1.27 ± 0.50 |
| $I_9$·HCl | 4.76 ± 3.78 |
| $I_{10}$·HCl | 4.45 ± 4.02 |
| $I_{11}$·HCl | 0.95 ± 0.29 |
| $I_{12}$·HCl | 1.96 ± 2.01 |

Example 14 Determination of Analgesic Activity by Rat Tail-Flick Test Under Thermal Radiation The tail tip of male SD rat was placed in the constant-temperature water bath of 55° C., the time was calculated until the tail tip flicked out of the water. The calculated time was recorded as the pre-administration basal pain threshold; Then the rats were randomly grouped to 5 animals in each group; Each mouse was administered by gavage, the tail tip of which was placed in the constant-temperature water bath of 55° C. 1 hour after administration. The time was calculated the tail tip flicked out of the water. The time calculated was recorded as the post-administration pain threshold; It was recorded as 100% of analgesia without the occurrence of tail-flicking in 15 seconds. The percentage of analgesia was calculated by comparison of the pain threshold before and after administration, and the calculation formula was as follows:

$$\text{analgesia \%} = \frac{\text{post-administration pain threshold} - \text{pre-administration pain threshold}}{15 \text{ s} - \text{pre-administration pain threshold}} \times 100\%$$

The $ED_{50}$ value was calculated using the bliss method. The results are shown in Table 2:

TABLE 2

Determination of analgesic activity by rat tail-flick test under thermal radiation

| Drug | $ED_{50}$ (mg/kg) |
|---|---|
| buprenorphine·HCl | >50 |
| ADP2·HCl | 8.06 ± 7.32 |
| $I_1$·HCl | 19.00 ± 7.29 |
| $I_2$·HCl | >50 |
| $I_3$·HCl | >50 |
| $I_4$·HCl | 14.52 ± 4.25 |
| $I_5$·HCl | 31.06 ± 10.91 |
| $I_6$·HCl | 18.04 ± 8.56 |
| $I_7$·HCl | 37.98 ± 19.70 |
| $I_8$·HCl | 4.01 ± 2.21 |

TABLE 2-continued

Determination of analgesic activity by rat tail-flick test under thermal radiation

| Drug | $ED_{50}$ (mg/kg) |
|---|---|
| $I_9 \cdot HCl$ | 13.73 ± 9.95 |
| $I_{10} \cdot HCl$ | 14.05 ± 8.20 |
| $I_{11} \cdot HCl$ | 2.98 ± 1.20 |
| $I_{12} \cdot HCl$ | 6.53 ± 5.20 |

Example 15 Evaluation of Drug Dependence by Rat Place Preference Test

SD rats (male, weight 160-180 g) were placed in a conditioned place preference training box with the partition door open, and the rats were allowed to stay in each box for determination of their residence time in 15 min, by which the natural tendency of the rats were judged. The rats were then randomized to 10 per group in term of their residence time in white box. The white box was the drug-side box, and the black box was the non-drug-side box. The rats were administered 3×$ED_{50}$ dose (hot plate method) of the test compounds by gavage, and immediately placed in the white box or black box for training 45 minutes, once a day for 9 consecutive days. On the 10th day, the rats were placed in the training box with the partition door open, and the residence time of the rats in the white box was measured within 15 minutes to evaluate the place preference effect of the rats. The experimental results are shown in Table 3:

TABLE 3

Test results of drug-induced place preference of rats

| Drug | Dose (mg/kg) | Residence time in drug-side box (Mean ± S, s) |
|---|---|---|
| solvent | | 106.59 ± 30.62 |
| buprenorphine•HCl | 35.5 | 277.56 ± 164.99 |
| ADP2•HCl | 7.8 | 240.23 ± 157.71 |
| $I_1$•HCl | 19.6 | 149.19 ± 36.88 |
| $I_4$•HCl | 13.8 | 137.77 ± 28.75 |
| $I_8$•HCl | 3.8 | 121.58 ± 33.98 |
| $I_{11}$•HCl | 2.9 | 134.52 ± 32.24 |
| $I_{12}$•HCl | 5.9 | 282.49 ± 196.72 |

Example 16 Evaluation of Drugs on Gastrointestinal Peristalsis by Mice Excretion Test Administered by Gavage with Activated Carbon Mice, half male and half female, fasted 8 hours before the experiment and free to drink water, were administered by gavage 3×$ED_{50}$ dose (hot plate method) of the test compounds; A suspension was prepared by 5% carbon powder and 10% methylcellulose, and administered to the mice at a dose of 0.2 ml/20 g 30 minutes after drug administration. 15 minutes after that, the mice were killed by cervical dislocation. The mice were laparotomized immediately, with the digestive tract completely removed from the cardia to the end of the rectum and tiled on a glass plate without traction, and the distance from the front of the suspension to the cardia was measured. The percentage of the distance and total length of the intestine was calculated. Ten animals were as a group. The inhibition percentage of activated carbon excretion after administration was compared by mean and standard deviation.

$$\text{Inhibition percentage (\%)} = \frac{\text{carbon migration distance of saline group} - \text{carbon migration distance after administration}}{\text{carbon migration distance of saline group}} \times 100\%$$

The experimental results are shown in Table 4:

TABLE 4

Inhibition of activated carbon excretion by drugs

| Drug | Dose (mg/kg) | Inhibition of activated carbon excretion (%) |
|---|---|---|
| solvent | | 0 |
| buprenorphine•HCl | 35.5 | 63.87 ± 2.16 |
| ADP2•HCl | 7.8 | 65.90 ± 3.39 |
| $I_1$•HCl | 19.6 | 36.31 ± 2.78 |
| $I_4$•HCl | 13.8 | 22.39 ± 2.00 |
| $I_8$•HCl | 3.8 | 34.50 ± 1.27 |
| $I_{11}$•HCl | 2.9 | 39.50 ± 10.80 |
| $I_{12}$•HCl | 5.9 | 77.14 ± 2.33 |

The invention claimed is:

1. A compound and a pharmaceutically acceptable salt thereof, wherein the compound is:

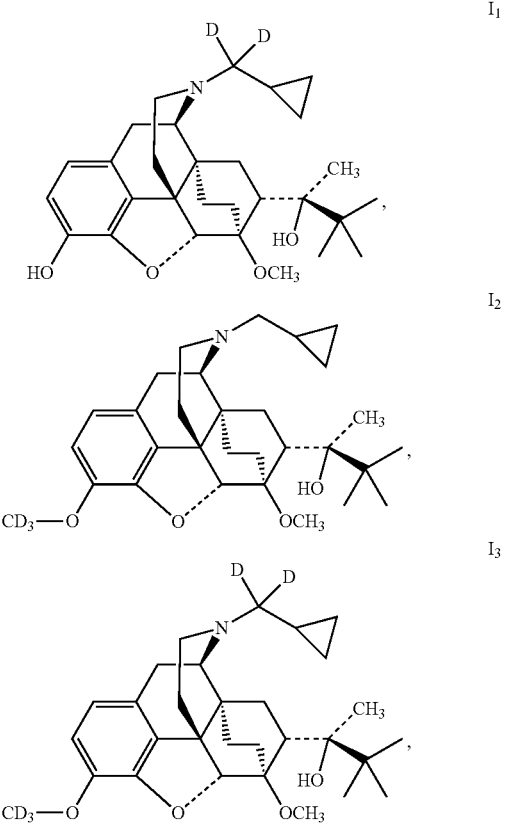

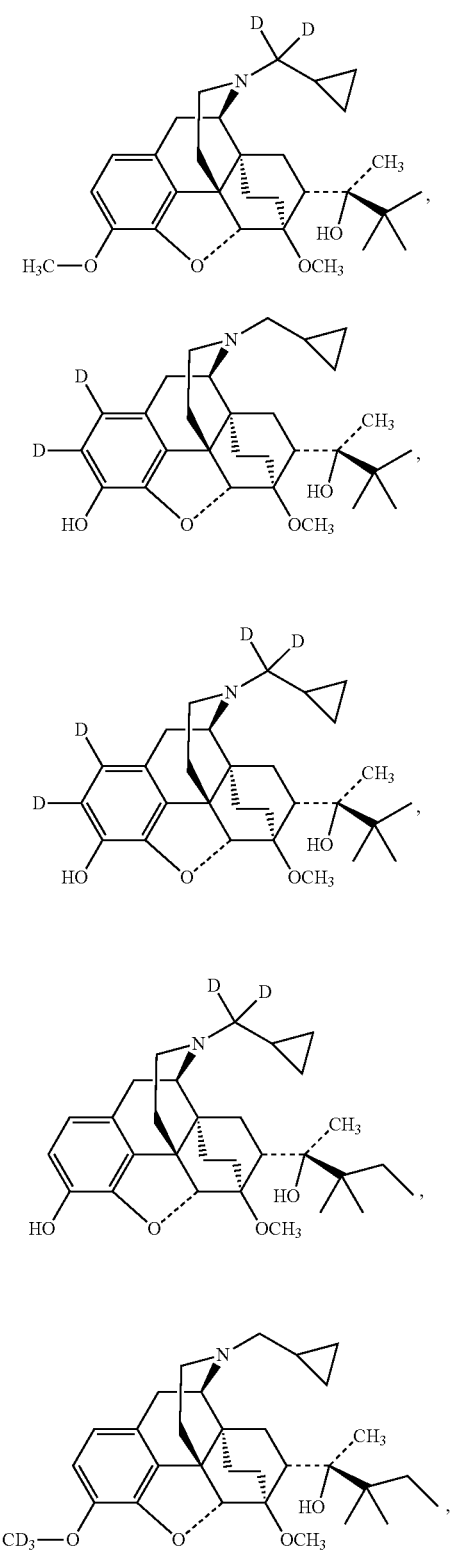

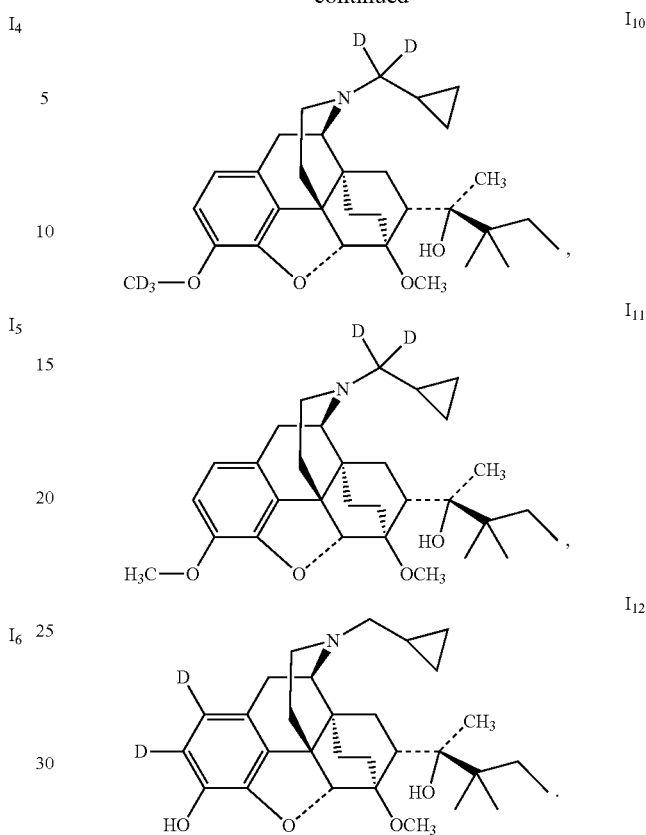

2. A pharmaceutical composition, comprising the compound or the pharmaceutically acceptable salt thereof according to claim 1 as an active ingredient, and one or more pharmaceutically acceptable carriers or excipients.

3. A method for treating algesic diseases, wherein the method comprises administering an effective amount of the compound or the pharmaceutically acceptable salt thereof according to claim 1 to a subject in need thereof.

4. A method for treating an drug addiction disease, wherein the method comprises administering an effective amount of the compound or the pharmaceutically acceptable salt thereof according to claim 1 to a subject in need thereof, wherein the drug addiction disease is chosen from cocaine-induced addiction, addition caused by methamphetamine-type drugs, opioid narcotics or drugs, alcohol addiction, smoking addiction, or ketamine-induced addiction.

5. A method for treating algesic diseases, wherein the method comprises administering an effective amount of the pharmaceutical composition according to claim 2 to a subject in need thereof.

6. A method for treating an drug addiction disease, wherein the method comprises administering an effective amount of the pharmaceutical composition according to claim 2 to a subject in need thereof, wherein the drug addiction disease is chosen from cocaine-induced addiction, addition caused by methamphetamine-type drugs, opioid narcotics or drugs, alcohol addiction, smoking addiction, or ketamine-induced addiction.

\* \* \* \* \*